(12) United States Patent
Kim et al.

(10) Patent No.: US 12,263,067 B2
(45) Date of Patent: Apr. 1, 2025

(54) WOUND CLOSURE DEVICES, KITS, AND RELATED METHODS

(71) Applicant: Chemence Medical, Inc., Alpharetta, GA (US)

(72) Inventors: Deog-Il Kim, Marietta, GA (US); Stephen Hynes, Roswell, GA (US); Jeff Roberson, Denver, NC (US)

(73) Assignee: Chemence Medical, Inc., Alpharetta, GA (US)

( * ) Notice: Subject to any disclaimer, the term of this patent is extended or adjusted under 35 U.S.C. 154(b) by 66 days.

(21) Appl. No.: 17/664,329

(22) Filed: May 20, 2022

(65) Prior Publication Data

US 2023/0372157 A1 Nov. 23, 2023

(51) Int. Cl.
*A61F 13/00* (2024.01)
(52) U.S. Cl.
CPC .... *A61F 13/00* (2013.01); *A61F 2013/00106* (2013.01); *A61F 2013/00225* (2013.01); *A61F 2013/00238* (2013.01)
(58) Field of Classification Search
CPC .............. A61F 13/00; A61F 13/00072; A61F 13/00076; A61F 13/00085; A61F 13/00089; A61F 13/00021; A61F 13/023; A61F 13/0246; A61F 13/0253; A61F 13/0259; A61F 13/60; A61F 2013/00106; A61F 2013/00225; A61F 2013/00238
USPC ................. 602/41–53, 54, 57, 900
See application file for complete search history.

(56) References Cited

U.S. PATENT DOCUMENTS

| | | |
|---|---|---|
| 4,614,183 A | 9/1986 | McCracken et al. |
| 5,429,592 A | 7/1995 | Jensen |
| 5,947,998 A | 9/1999 | Cartmell et al. |
| 5,951,505 A | 9/1999 | Gilman et al. |
| 5,998,694 A | 12/1999 | Jensen et al. |
| 6,159,497 A | 12/2000 | LaPrade et al. |
| 6,440,513 B1 | 8/2002 | Kibele et al. |
| 7,122,712 B2 | 10/2006 | Lutri et al. |
| 7,164,054 B2 | 1/2007 | Mori et al. |
| 7,563,941 B2 | 7/2009 | Ebner et al. |
| 8,168,851 B2 | 5/2012 | Nakahara et al. |
| D692,149 S | 10/2013 | Uematsu |

(Continued)

FOREIGN PATENT DOCUMENTS

| | | | |
|---|---|---|---|
| EP | 3695819 B1 | 3/2022 | |
| KR | 101361040 B1 | 2/2014 | |
| WO | WO-2017052549 A1 * | 3/2017 | ....... A61F 13/00085 |

OTHER PUBLICATIONS

PCT/US2023/023155, "International Search Report and Written Opinion", Aug. 7, 2023, 15 pages.

*Primary Examiner* — Caitlin A Carreiro
(74) *Attorney, Agent, or Firm* — Kilpatrick Townsend & Stockton LLP

(57) ABSTRACT

Wound closure devices and related methods. In one example, a wound closure device includes a release liner and several wound closure meshes held in a removable fashion to the release liner. The release liner includes a main body and several tabs, with the tabs secured in a detachable fashion to the main body. Each wound closure mesh is held in a removable fashion to the main body of the release liner and at least one of the tabs, with the tab including a portion that extends outwardly from an outer perimeter of the mesh to which it is held.

21 Claims, 16 Drawing Sheets

(56) References Cited

U.S. PATENT DOCUMENTS

| | | | |
|---|---|---|---|
| 9,439,873 B2 | 9/2016 | Aigle et al. | |
| 9,655,622 B2 | 5/2017 | Jonn et al. | |
| D848,624 S | 5/2019 | Quintero | |
| D854,171 S | 7/2019 | Quintero | |
| 10,398,800 B2 | 9/2019 | Jonn et al. | |
| 10,398,802 B2 | 9/2019 | Jonn et al. | |
| 10,434,211 B2 | 10/2019 | Jonn et al. | |
| 10,470,934 B2 | 11/2019 | Quintero | |
| 10,478,346 B2 | 11/2019 | Knutson | |
| 10,639,118 B2 | 5/2020 | McGuire | |
| 10,687,986 B2 | 6/2020 | Quintero | |
| 10,849,704 B2 | 12/2020 | Galbierz et al. | |
| D907,217 S | 1/2021 | Quintero | |
| 2005/0182443 A1 | 8/2005 | Jonn et al. | |
| 2006/0265005 A1 | 11/2006 | Beese | |
| 2010/0178322 A1 | 7/2010 | Ameyama et al. | |
| 2010/0318013 A1 | 12/2010 | Fabo et al. | |
| 2013/0152944 A1 | 6/2013 | Okada et al. | |
| 2014/0121620 A1 | 5/2014 | Hung | |
| 2015/0257938 A1 | 9/2015 | Pensler | |
| 2018/0085260 A1* | 3/2018 | Quintero | A61F 13/00085 |
| 2018/0092779 A1 | 4/2018 | Theunissen et al. | |
| 2018/0289921 A1* | 10/2018 | Burkholz | A61M 25/00 |
| 2019/0167373 A1 | 6/2019 | McGuire | |
| 2019/0240074 A1 | 8/2019 | Quintero | |
| 2019/0350873 A1 | 11/2019 | Ramjit et al. | |
| 2019/0381206 A1 | 12/2019 | Jonn et al. | |
| 2019/0381207 A1 | 12/2019 | Jonn et al. | |
| 2020/0315858 A1 | 10/2020 | Quintero | |

\* cited by examiner

WOUND CLOSURE DEVICES, KITS, AND RELATED METHODS

RELATED FIELDS

Wound closure devices, kits, and related methods, particularly wound closure devices utilizing one or more wound closure meshes in conjunction with a topically applied liquid skin adhesive.

BACKGROUND

EXOFIN FUSION® is a commercially available wound closure system that includes one or two self-adhering mesh patches and a liquid, topical, skin adhesive. The mesh patches are coated on a single side with a pressure-sensitive adhesive (PSA), and in use, the PSA-coated side directly contacts the skin to temporarily adhere the mesh patch(es) to the skin. In use, the self-adhering mesh patch is applied over and fully covering a wound, with the PSA-coated side of the mesh patch contacting the skin. Next, the liquid, topical skin adhesive is applied over the exposed surface of the mesh patch and allowed to polymerize, which may take in some uses approximately 45-60 seconds. Once polymerized, the adhesive creates a watertight, microbial barrier allowing patients to quickly resume normal daily activities like showering. The mesh and adhesive create a strong seal. The shape of the mesh distributes tension along the wound, preventing skin gaps from forming.

The mesh patches included with EXOFIN FUSION® and similar wound closure devices are typically configured for closing larger incisions, e.g. incisions of up to 20 cm, 28 cm, or 58 cm. Some procedures, such as laparoscopic and other minimally invasive surgical procedures, utilize one or several smaller incisions. There is a need for a wound closure system that can provide the benefits of the EXOFIN FUSION® wound closure system for use in a laparoscopic or similar surgical procedures in which one or more relatively small incisions will require closure.

SUMMARY

We have developed wound closure devices, kits, and related methods that are optimized for use in procedures involving one or more relatively small incisions.

In one example, a wound closure device includes: (a) a release liner, the release liner having a main body and several of tabs, in which the tabs are secured in a detachable fashion to the main body; and (b) several wound closure meshes, in which each mesh is held in a removable fashion to the main body and at least one of the tabs, the tabs including portions that extend outwardly from an outer perimeter of the mesh to which each tab is held.

In some implementations, each mesh may be held in a removable fashion to the main body and at least two of the tabs, both tabs including portions that extend outwardly from the outer perimeter of the mesh to which they are held.

In some implementations, the main body of the release liner includes several arms, with each mesh being held in a removable fashion to one of the arms.

In some implementations, each arm has a wider portion and at least one thinner portion.

In some implementations, each mesh is held on the wider and thinner portions of the arm.

In some implementations, each mesh includes a central area, and the arms of the release liner extend across the central areas of the meshes.

In some implementations, the tabs associated with a mesh extend along the sides of that mesh.

In some implementations, the wound closure device is configured such that each of the meshes can be removed from the main body while retaining the two tabs extending along the sides of the mesh.

In some implementations, the meshes are self-adhering mesh patches.

In another example, a wound closure kit includes: (a) a wound closure device, such as any of the wound closure devices described in any of the previous examples; and (b) an adhesive applicator containing a liquid, topical skin adhesive.

In some implementations, the wound closure device and the adhesive applicator is in a sealed package containing the wound closure device and adhesive applicator in a sterile fashion.

In another example, a wound closure method includes: (1) selecting a wound closure mesh from a wound closure device, such as any of the wound closure devices described in any of the previous examples; (2) removing the selected wound closure mesh from the main body using at least one tab removably held to the selected wound closure mesh; (3) positioning the selected wound closure mesh on a wound; and (4) removing the at least one tab from the first wound closure mesh.

In some implementations, removing the selected wound closure mesh from the main body includes: (a) bending the wound closure device to expose an edge of a tab removably held to the selected wound closure mesh; and (b) pulling the exposed edge of the tab away from the main body to separate the tab and the selected wound closure mesh from the wound closure device.

In some implementations, after positioning the selected wound closure mesh on the wound, the tab associated with the wound closure mesh is pulled on to approximate the wound.

In some implementations the method also includes applying a liquid adhesive to the first wound closure mesh after approximating the wound.

DETAILED DESCRIPTION

Wound Closure Device

FIGS. 1-7 show an example of a wound closure device 100. The wound closure device illustrated in FIGS. 1-7 is exemplary only, and may be modified or otherwise changed without departing from the scope or spirit of our invention.

The wound closure device 100 includes a release liner 102, with several wound closure meshes 104 releasably held on the release liner 102. In this example, the wound closure device 100 includes four separate wound closure meshes 104, although in other implementations, the wound closure device may include more or less meshes.

In this particular example, the release liner 102 is generally planar and rectangular, although other shapes and configurations are also possible. In one implementation, the release liner 102 may be paper (78 lb. basis weight) coated on both sides with silicone, while in other implementations, the release liner 102 may be any other material that is suitable for releasably holding the wound closure meshes 104.

In this particular example, the wound closure meshes 104 are also generally planar and rectangular, although other shapes and configurations are also possible. In one implementation, the wound closure meshes 104 may be made from synthetic or natural materials which can be woven or non-woven fabrics. The meshes 104 may be nylon, polyester, polypropylene or polyethylene, polyamide and cottons. The mesh net-shapes can be square or rhombus and the net-sizes may be from 0.5 to 2 mm. The preferred net-sizes in some implementations are from 0.8 to 1.3 mm. The wound closure meshes 104 may be coated with or otherwise associated with a pressure sensitive adhesive suitable for holding the meshes 104 on the release liner 102 in a removable fashion, and also for temporarily holding the meshes 104 in place on a patient's skin, as discussed in further detail below. In some implementations, the pressure sensitive adhesive may be a rubber-based, silicone-based, or acrylic-based adhesive. In one implementation, the meshes 104 are coated on a single side with a pressure sensitive adhesive, and in use, the PSA-coated side directly contacts the skin to temporarily adhere the mesh to the skin. In some implementations, the PSA is only coated on a portion of the mesh, such as on 20-80% of the area on one side of the mesh, or 30-65% of the area on one side of the mesh.

In the example shown in FIGS. 1-7, the PSA-coated side of the meshes are the side that contacts the release liner 102.

Figure 1:
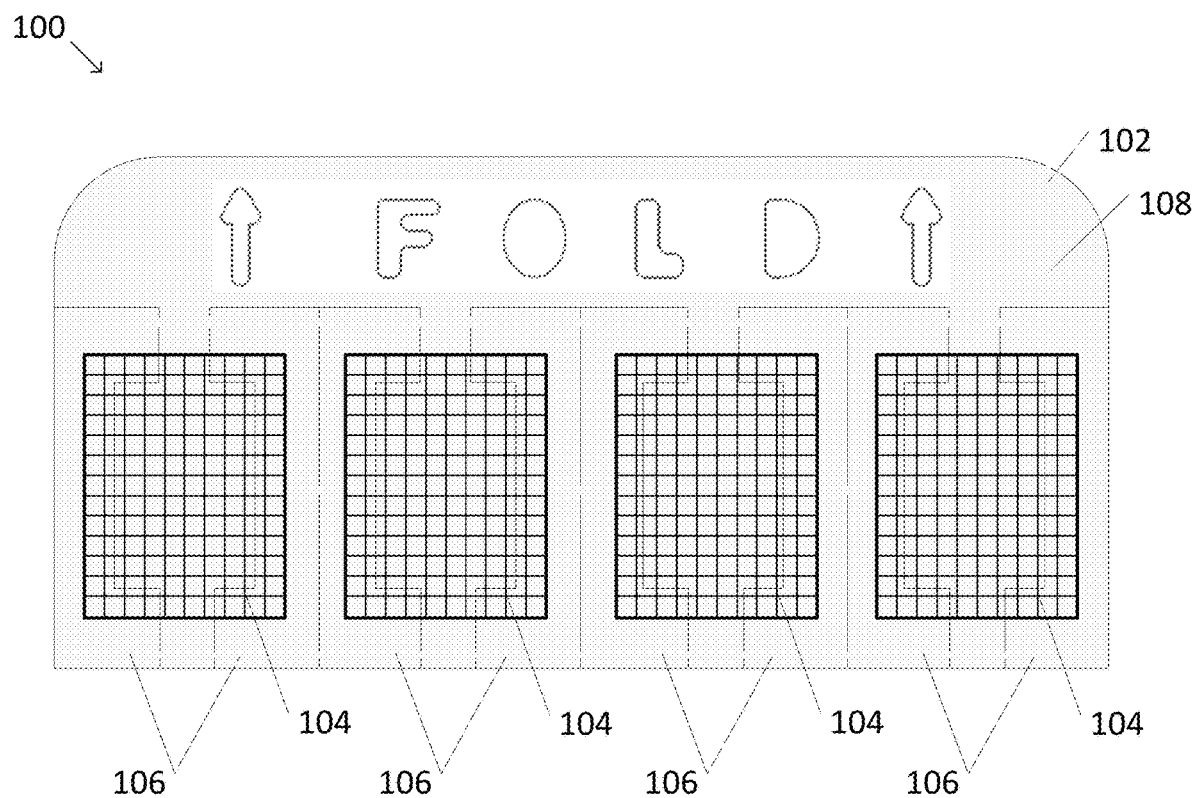
FIG. 1 shows one example of a wound closure device.
Figure 2:
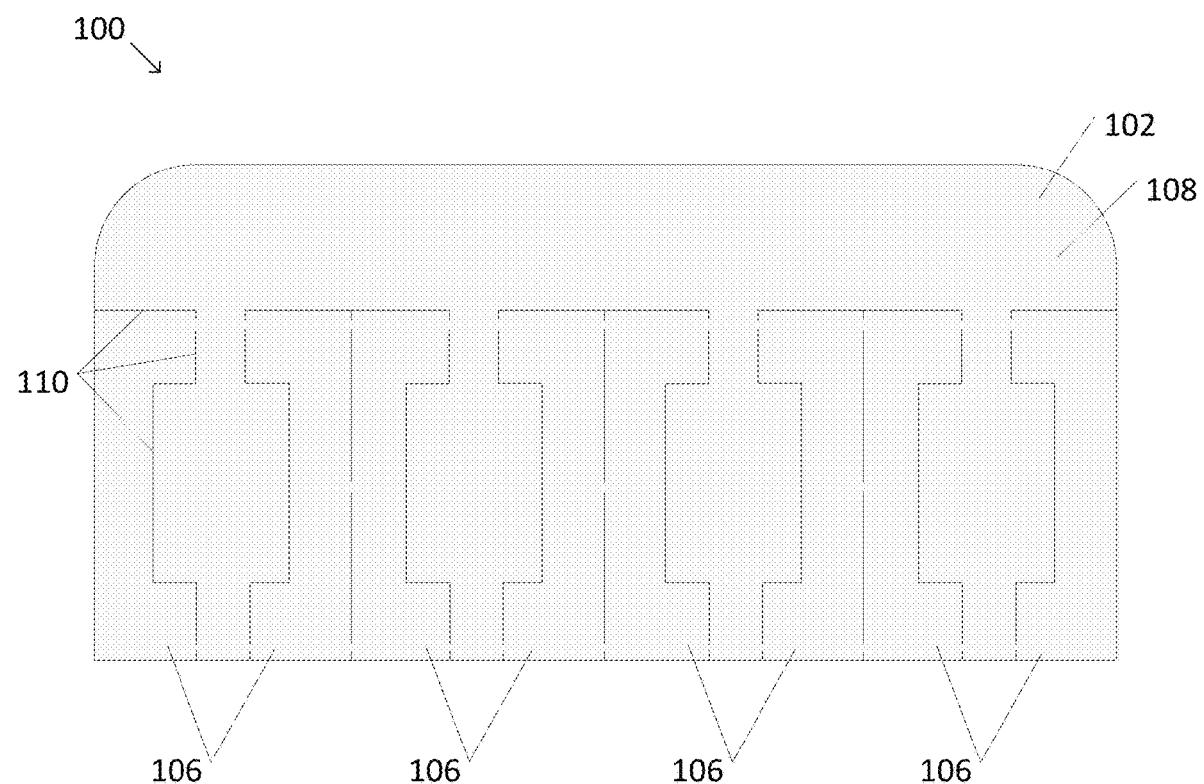
FIG. 2 shows the wound closure device of FIG. 1 from the opposite side as FIG. 1.
Figure 3:
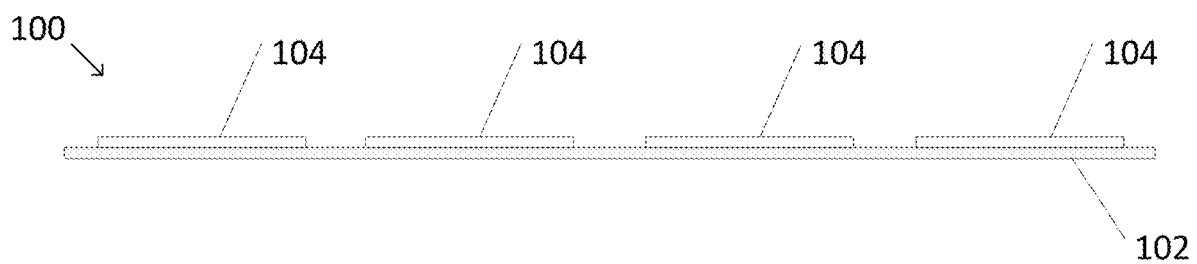
FIG. 3 shows the wound closure device of FIG. 1 in cross-section.
Figure 4:
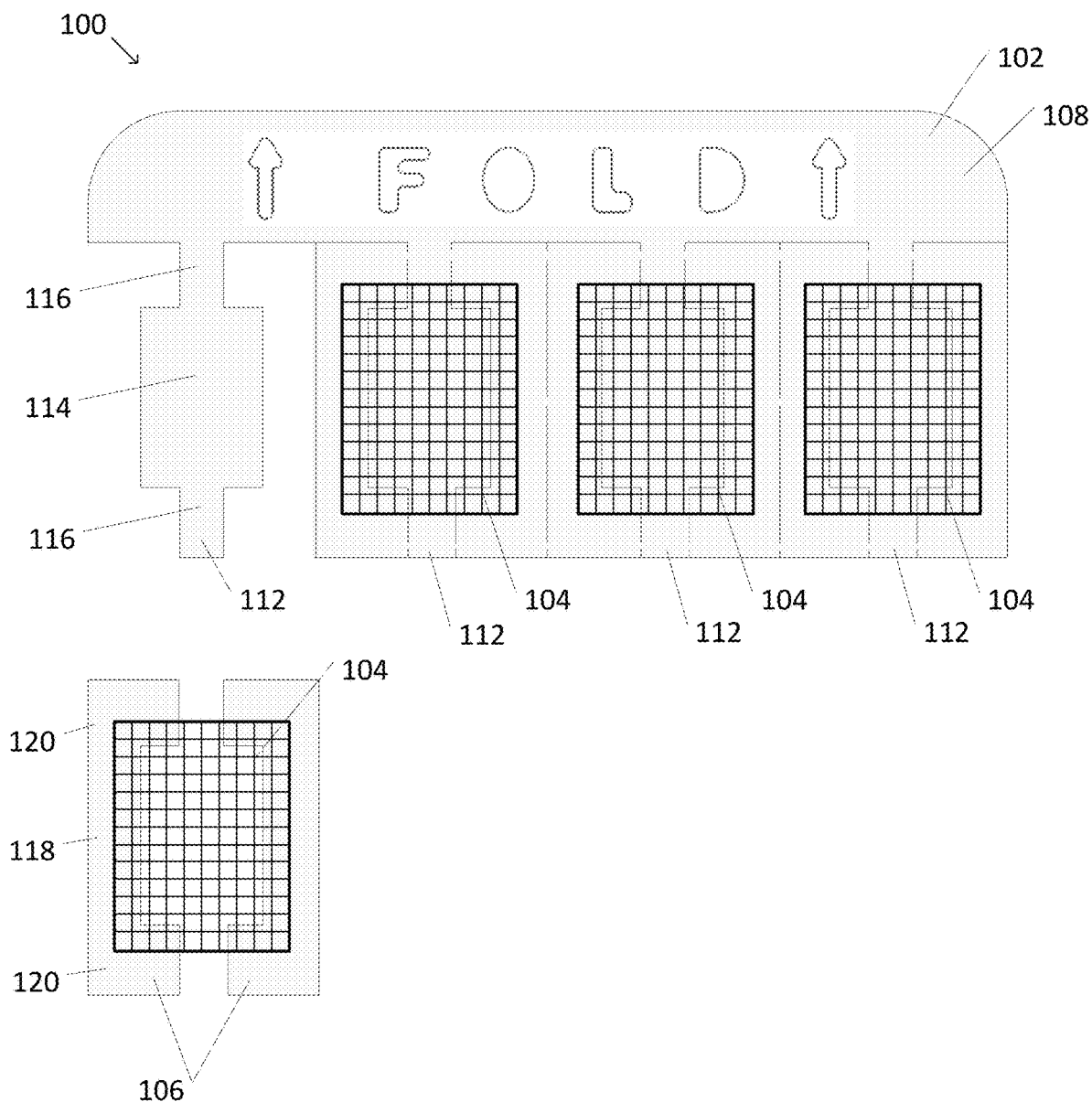
FIG. 4 shows the wound closure device of FIG. 1 with one of the meshes and its associated tabs removed from the rest of the device.
Figure 5:
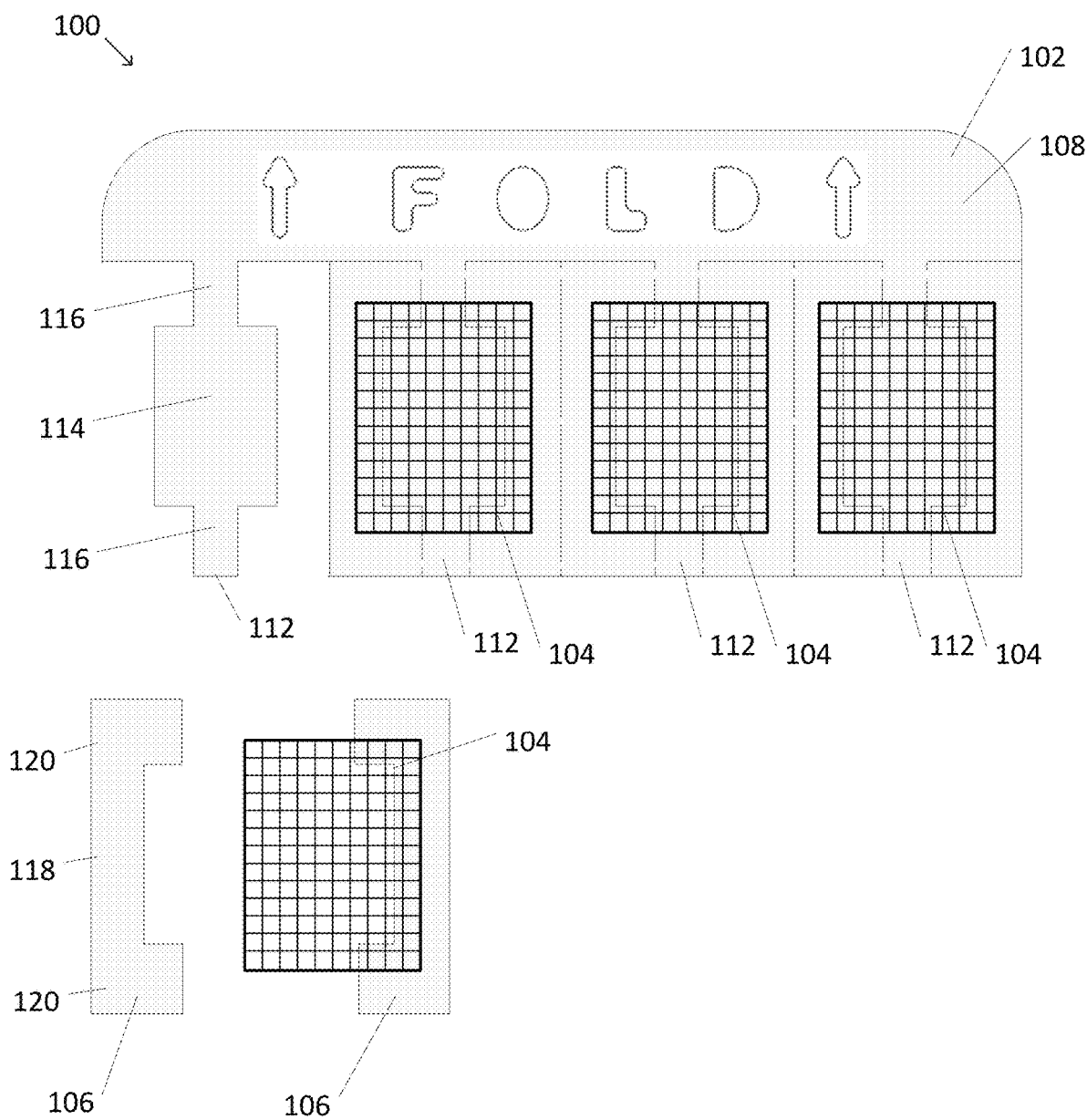
FIG. 5 shows the wound closure device of FIG. 1 with one of the meshes and its associated tabs removed from the rest of the device, and one of the tabs removed from the mesh.
Figure 6:
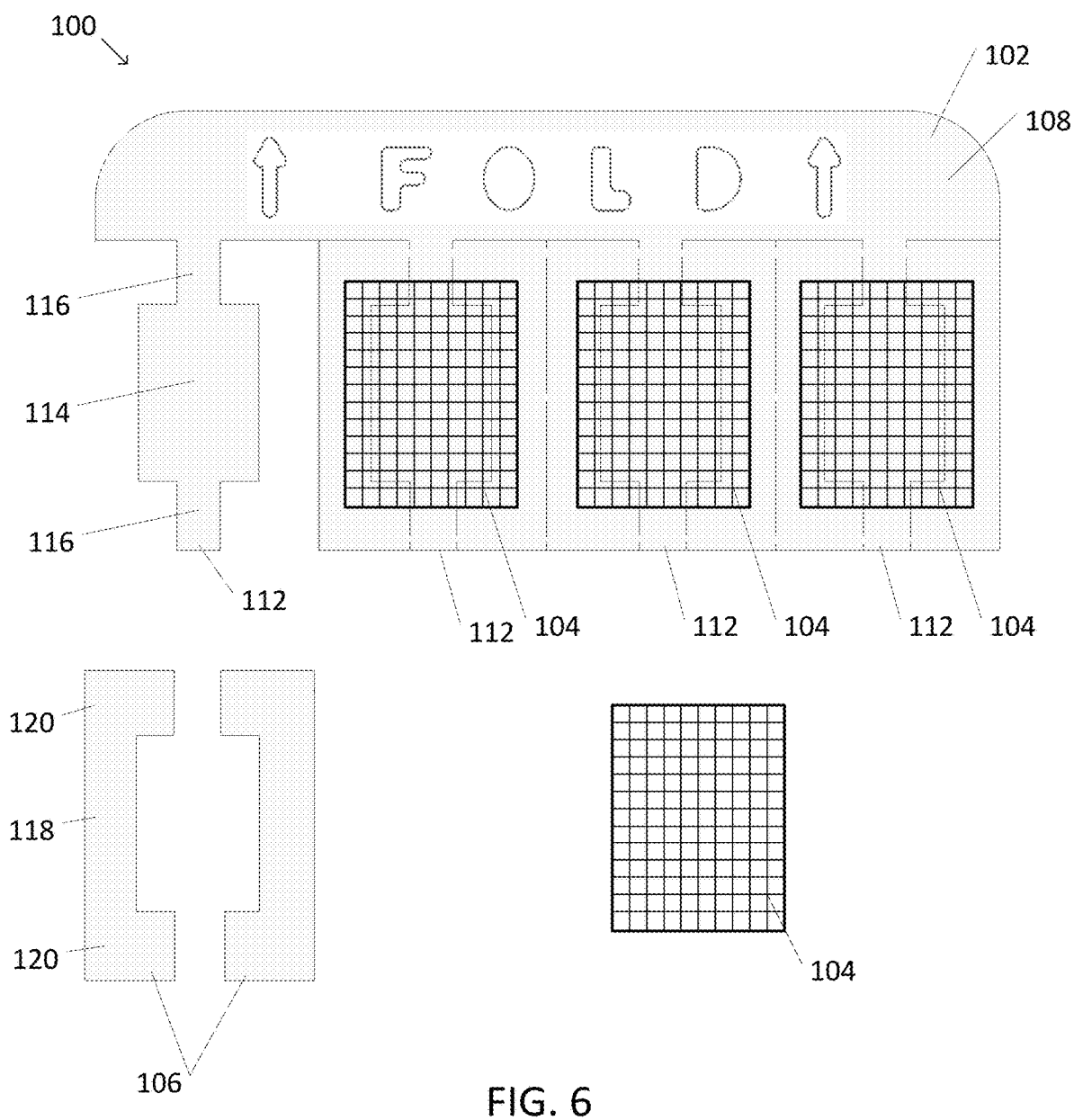
FIG. 6 shows the wound closure device of FIG. 1 with one of the meshes and its associated tabs removed from the rest of the device, and both of the tabs removed from the mesh.
Figure 7:
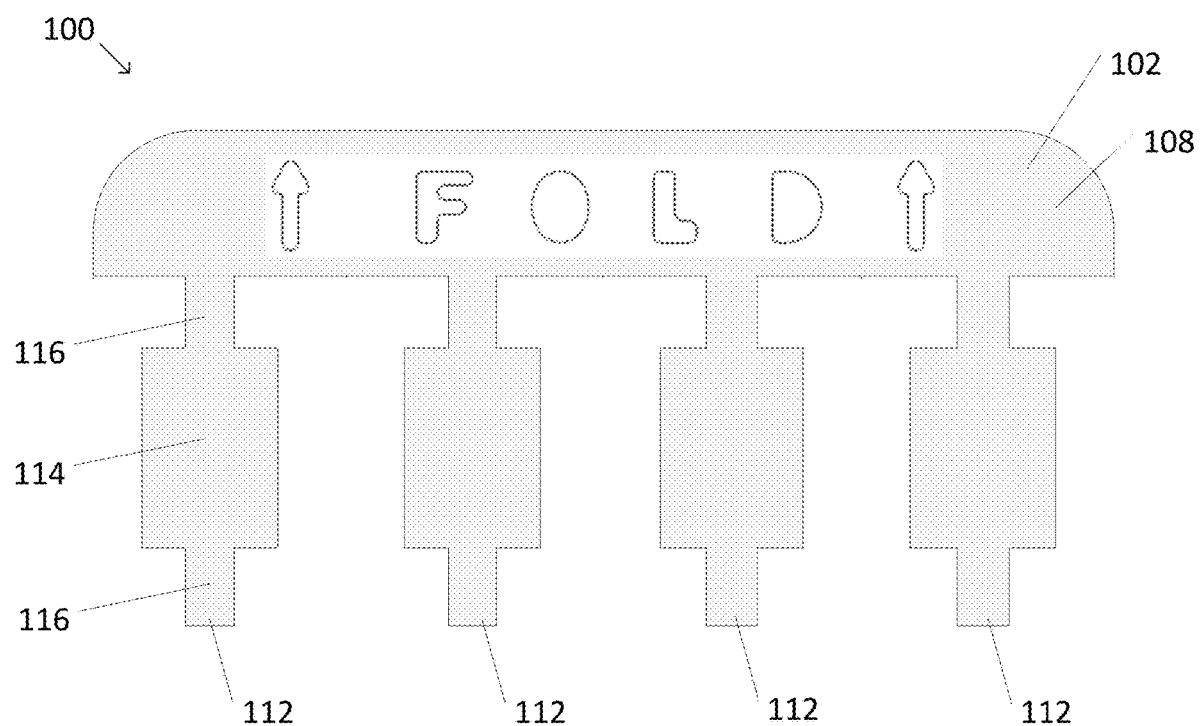
FIG. 7 shows a main body of the release liner of the wound closure device of FIG. 1 after all of the meshes and their associated tabs have been removed.

In the example shown in FIGS. 1-7, the wound closure meshes 104 are releasably held on one side of the release liner 102, as shown in FIGS. 1-3. The wound closure meshes 104 and associated tabs 106 of the release liner 102 may be removed as a unit from the main body 108 of the release liner 102. FIG. 4 shows the wound closure device 100 with one of the wound closure meshes 104 and two release liners 106 removed as a unit from the rest of the device.

The release liner 102 is scored along score lines 110 (seen e.g. FIG. 2), which allow the tabs 106 to be separated from the main body 108. In some implementations, the meshes 104 may also be scored (e.g. at the corners) so that they shape of the meshes 104 may be altered in use.

The release liner 102 is configured so that when a mesh 104 and its associated tabs 106 are removed from the main body 108 of the release liner 102, portions of the tabs 106 extend outwardly from an outer perimeter of the mesh 102 while a central area of the mesh 102 is open and uncovered by the tabs 106. The portions of the tabs 106 extending outwardly from the outer perimeter of the mesh 102 facilitate handling of the mesh 102 without requiring direct contact with its pressure sensitive adhesive (which could become undesirably stuck on a surgical glove). As can be seen best in FIGS. 4 and 5, each tab 106 extends along three sides of the mesh 102. In this particular example, each tab 106 extends along the entire length of one of the long sides of the mesh 102, and extends along part of the length of two of the shorter sides of the mesh 102.

Leaving the central area of the mesh 104 open and uncovered facilitates visualization and alignment of the mesh 104 over a wound, as discussed in more detail below.

The score lines 110 in the release liner 102 define the shape of the tabs 106 and the shape of the remainder of the main body 108 of the release liner 102 after the tabs 106 are removed. As can be seen best in FIGS. 4-7, the main body 108 of the release liner 102 includes several arms 112. The arms 112 have wider 114 and narrower 116 portions corresponding the narrower 118 and wider 120 portions of the tabs 106 respectively. The wider 114 portion of the arms 112 corresponds to the central area of the mesh 104 when it is releasably held on the release liner 102. The arms 112 extend entirely across the mesh 104 when the mesh 104 is releasably held on the main body of the release liner 104.

Wound Closure Kit

Figure 8:
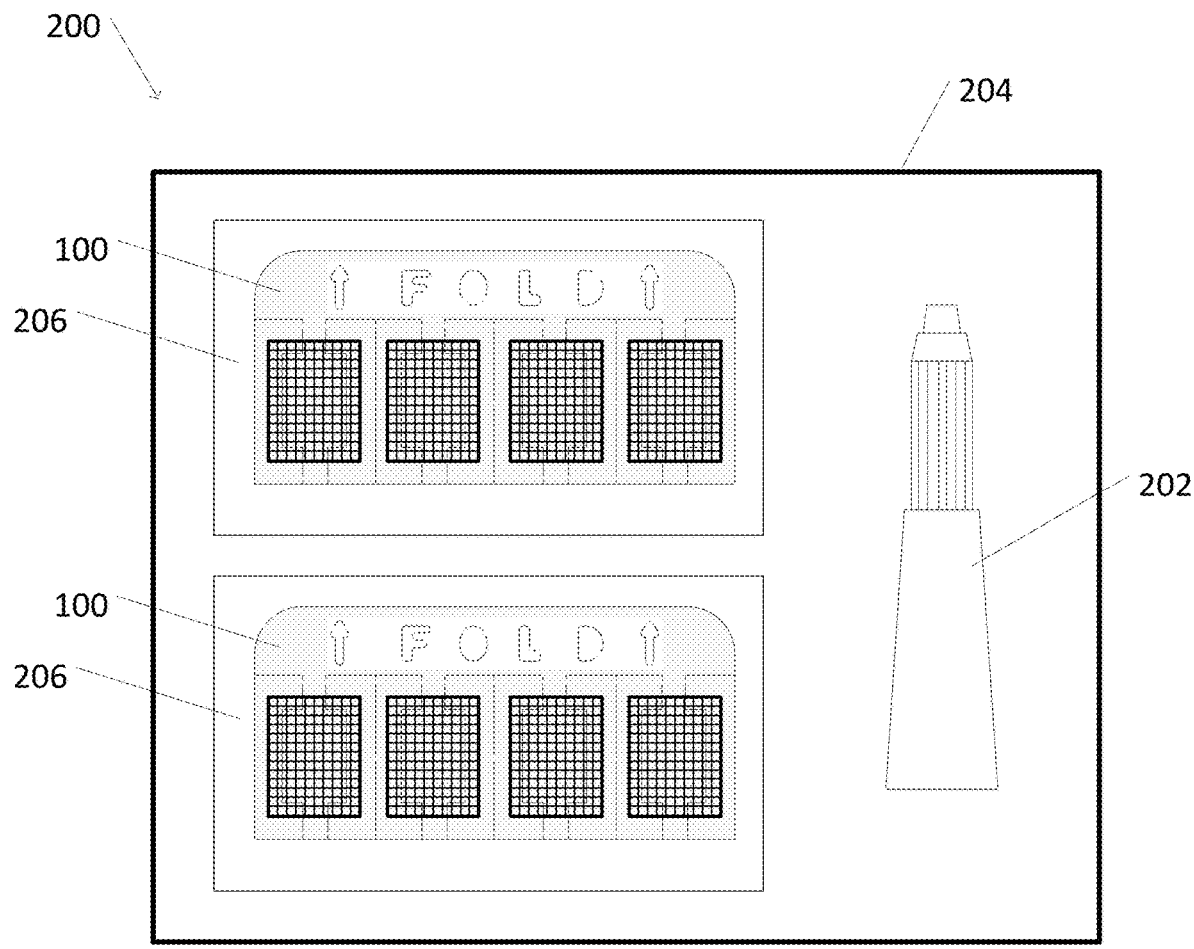
FIG. 8 shows an example of a wound closure kit.

FIG. 8 schematically illustrates a wound closure kit 200. The wound closure kit 200 illustrated in FIG. 8 is exemplary only, and may be modified or otherwise changed without departing from the scope or spirit of our invention.

The wound closure kit 200 may include any number of wound closure devices (in this example, two wound closure devices 100) and one or more adhesive applicators 202 containing a liquid, topical skin adhesive. In this example, each wound closure device 100 is the same as the wound closure device 100 shown in FIGS. 1-7 and described above, although in other implementations they may be configured differently. In the example shown the two wound closure devices 100 are identical to one another, although in other implementations, they do not need to be identical.

In this example, the wound closure kit 200 is enclosed in a sealed package (e.g. sterile tray 204) containing the wound closure devices 100 and adhesive applicator 202 in a sterile fashion, and the wound closure devices 100 are individually wrapped in envelopes 206. In other implementations, the wound closure devices 100 are not wrapped in envelopes.

Wound Closure Method

FIGS. 9-21 show one example of a wound closure method. The method illustrated in FIGS. 9-21 is exemplary only, and may be modified or otherwise changed without departing from the scope or spirit of our invention.

Figure 9:
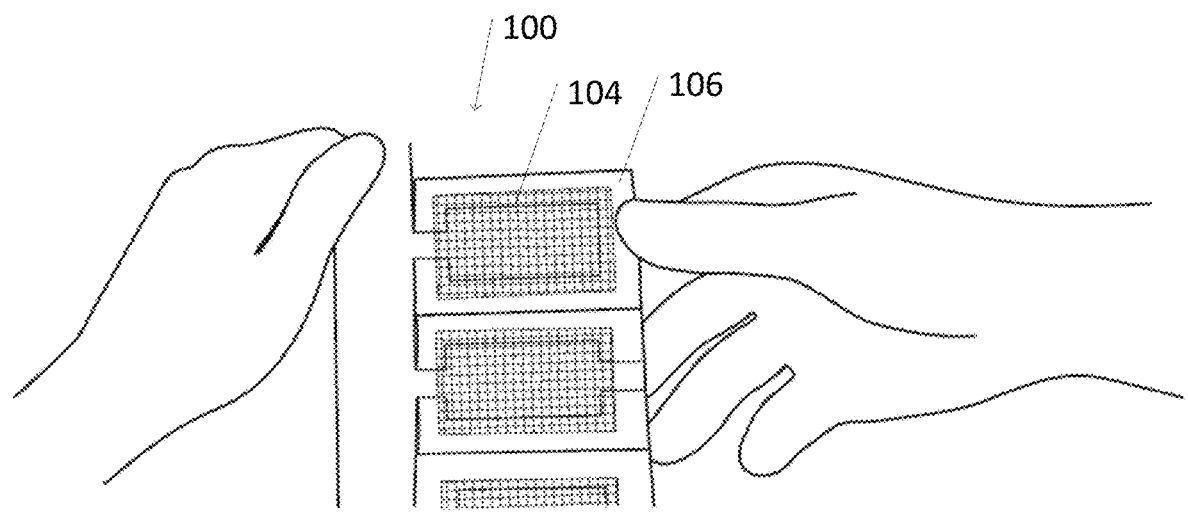
FIGS. 9-20 show an example of a wound closure method.

FIG. 9 shows selecting a wound closure mesh 104 from a wound closure device 100. Similar to the wound closure device 100 shown in FIGS. 1-7, the wound closure device 100 shown in FIG. 9 includes a release liner with a main body and several tabs secured in a detachable fashion to the main body, and also includes several wound closure meshes held in a removable fashion to the main body and the tabs. As shown in FIG. 9 (among other figures), the tabs (e.g. tab 106) extend outwardly from the wound closure meshes so that they can be handled without contacting the adhesive on the meshes.

The configuration of the release liner, including the tabs and main body, facilitate easy removal of a selected mesh from the release liner, and easy handling of the mesh when using it to facilitate wound closure.

Figure 10:
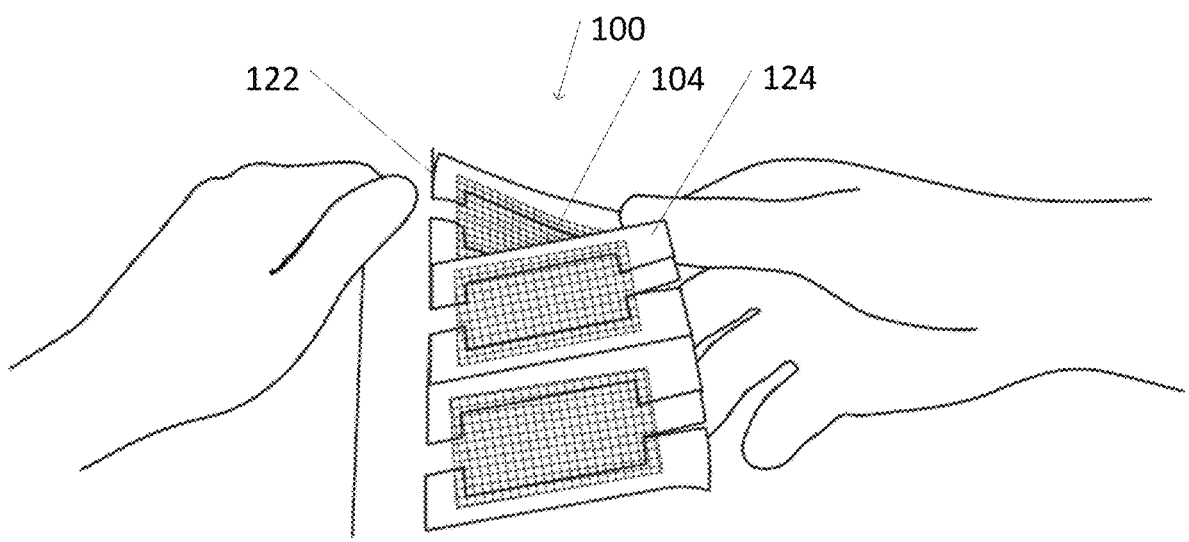
Figure 11:
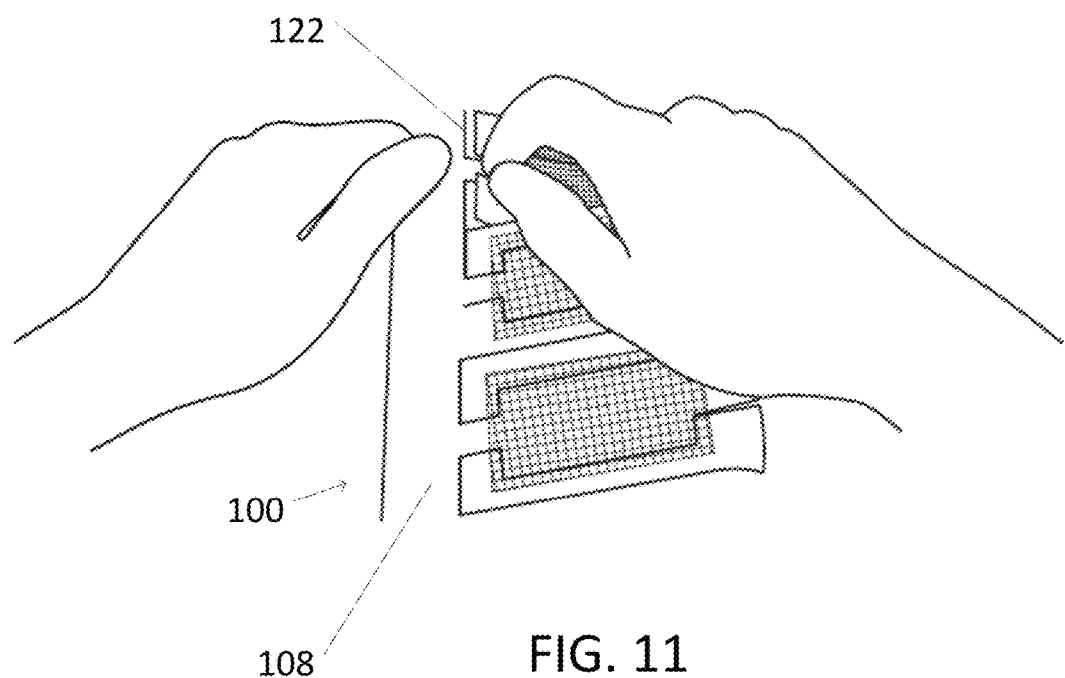
Figure 12:
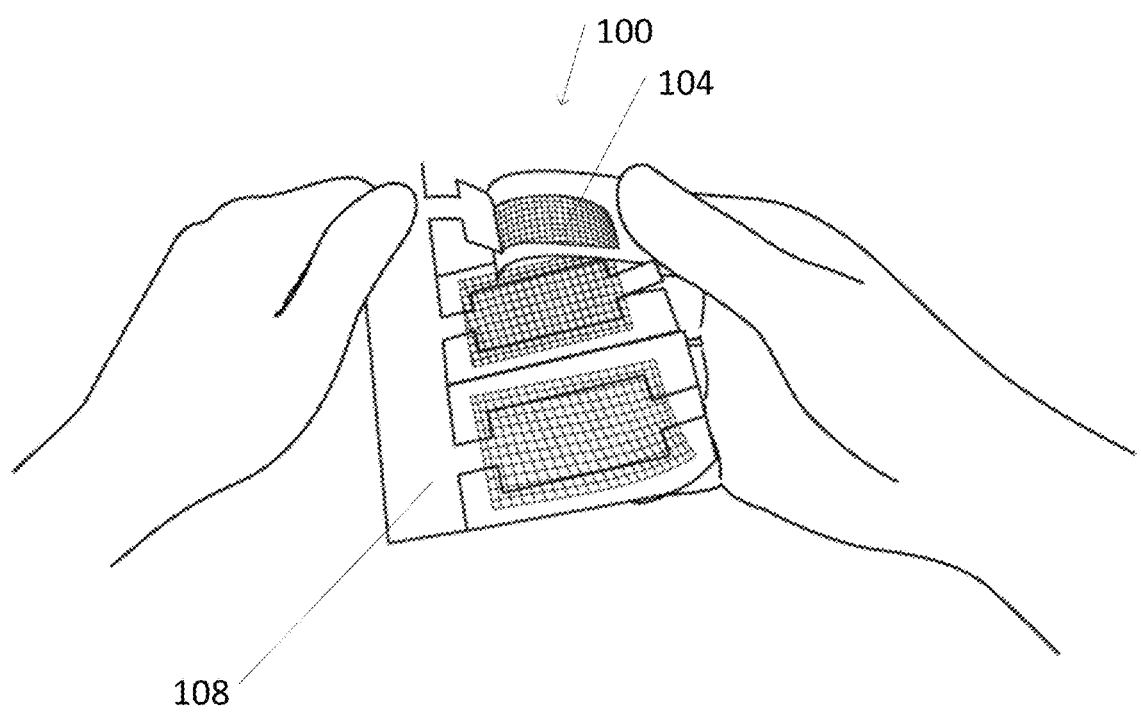
Figure 13:
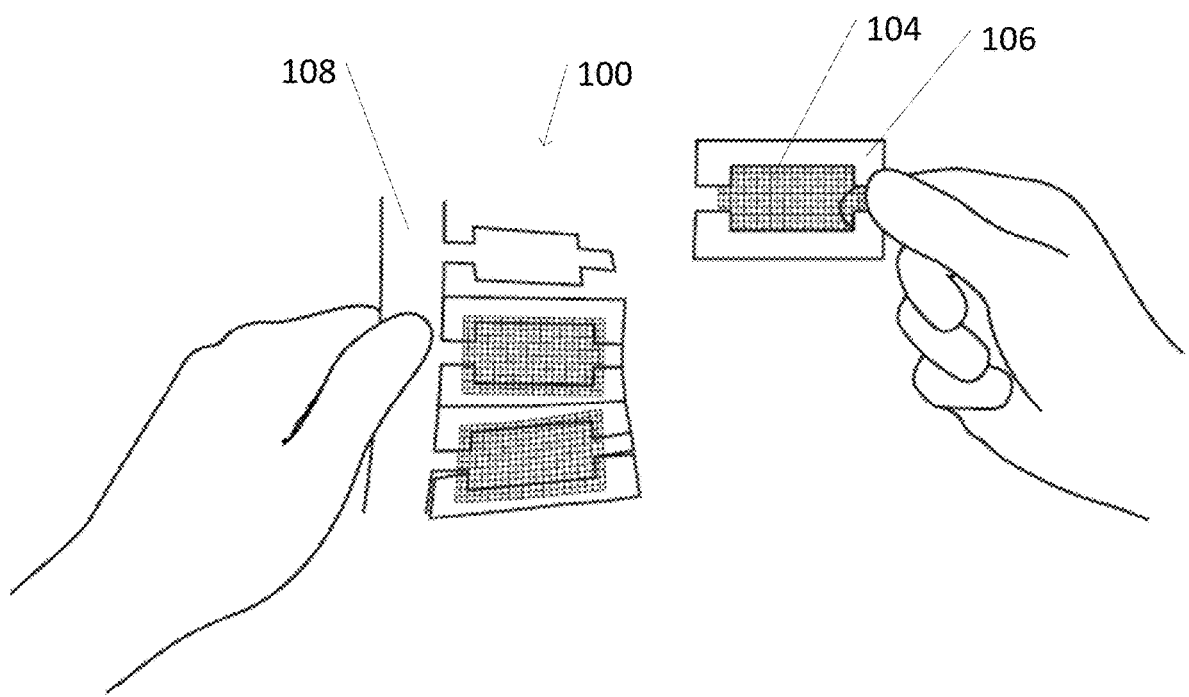

FIGS. 10-13 show removing the selected wound closure mesh 104 from the wound closure device 100. As shown in FIG. 10, the user may first bend the wound closure device 100 so that an edge 122 of one or more of the tabs is exposed. The wound closure device 100 may be bent along a line generally corresponding to the edge 122. As also shown in FIG. 10, bending the wound closure device 100 at the selected portion may separate a tab from an adjacent tab 124 of the device 100. As shown in FIGS. 11-13, the exposed edge 122 may be grasped by the user and pulled away from the main body 108 of the release liner, so that the tabs 106 and associated mesh 104 are separated from the main body 108 of the wound closure device 100.

Figure 14:
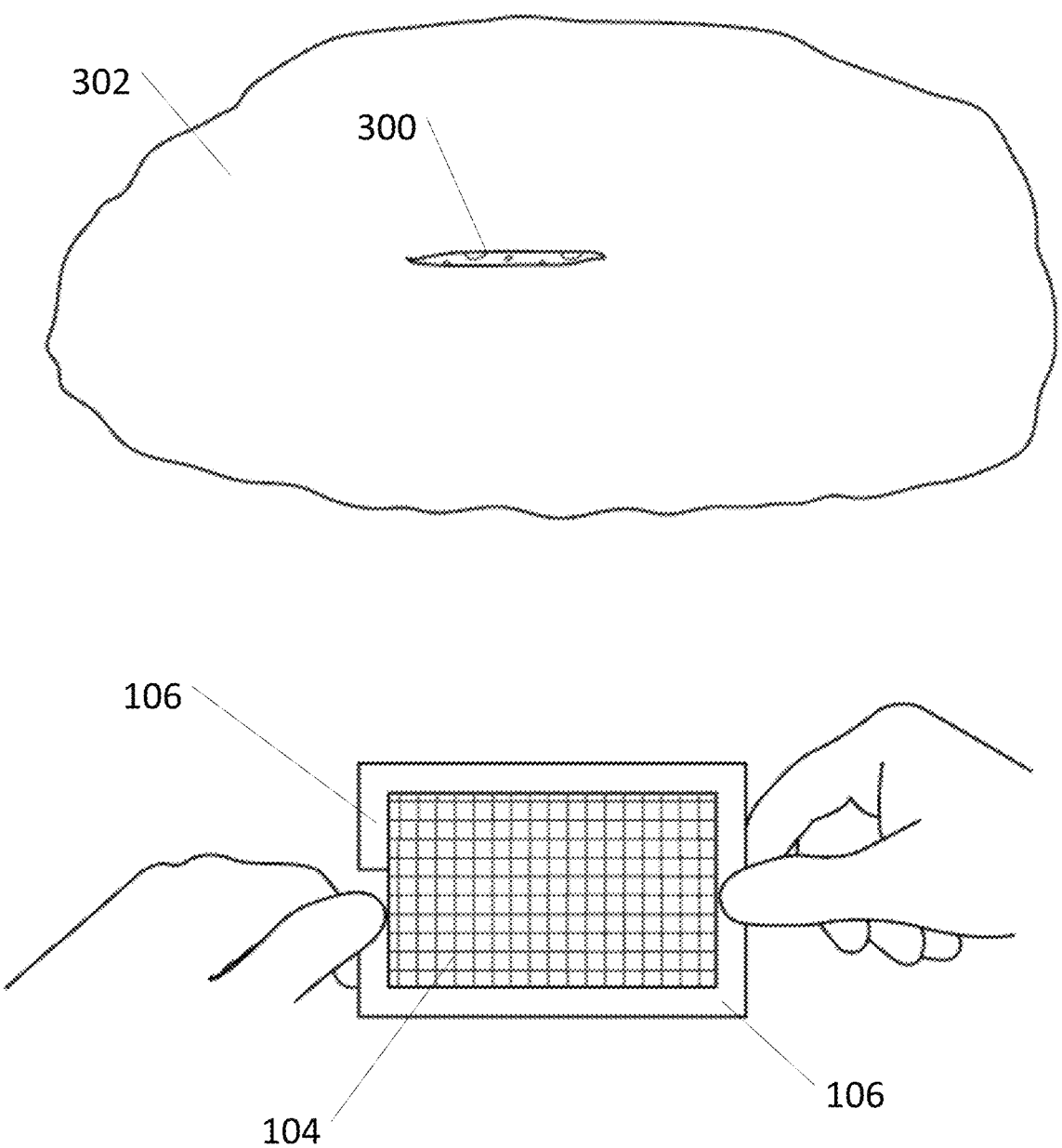

FIGS. 14-17 show positioning the wound closure mesh 104 on a wound 300 in a patient's skin 302. As shown in FIG. 14, the wound closure mesh 104 may be continued to be held by portions of the tabs 106 extending outwardly from the mesh 104 as the wound closure mesh is positioned over and onto the wound 300, to avoid or at least limit contact between the user's hands and the adhesive on the mesh 104.

Figure 15:
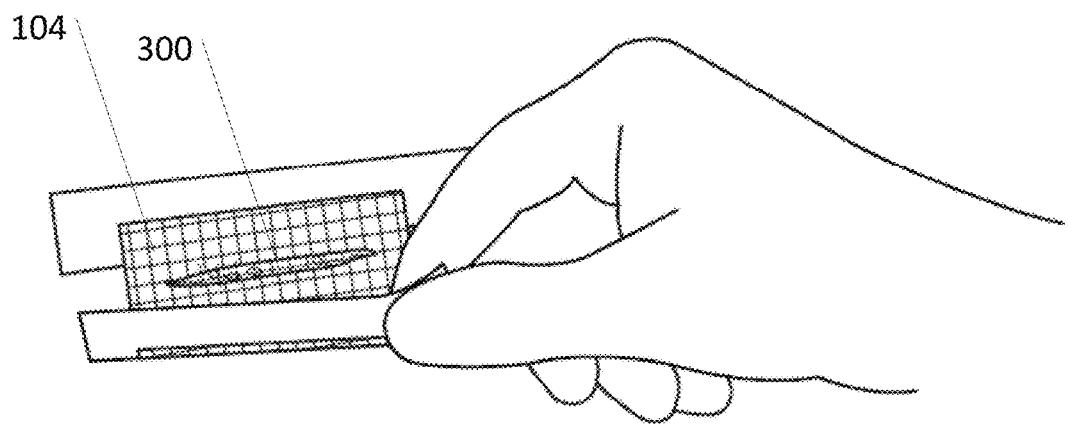
Figure 16:
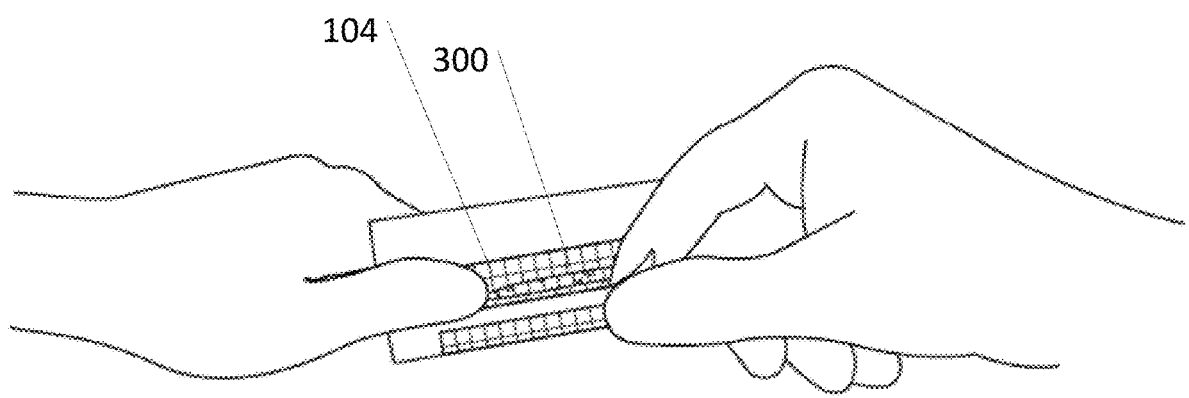
Figure 17:
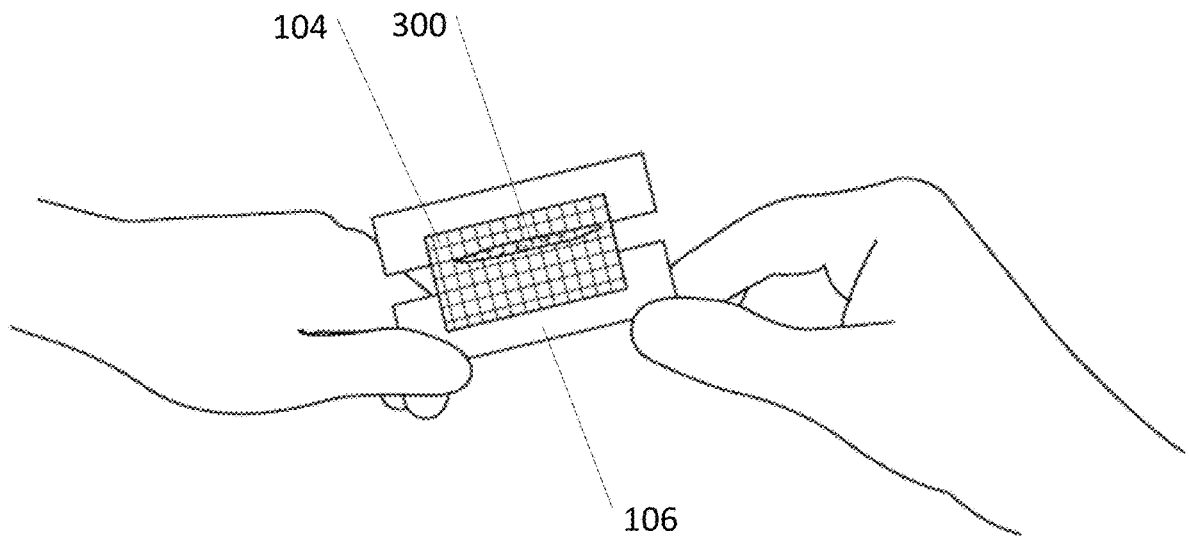

As shown in FIGS. 15-17, the wound closure mesh 104 may initially be placed over and primarily in contact with the patient's skin on one side of the wound 300, with the pressure sensitive adhesive coated side of the mesh 104 in contact with the patient's skin. FIG. 17 shows approximation of the wound 300, with the user gently pulling on the tab 106 on the side of the mesh 104 that has not yet been brought fully into contact with the patient's skin, so that the edges of the wound 300 may be drawn together and closed. In the example shown, the mesh 104 is positioned on the patient's skin such that the tabs 106 are on the underside of the mesh 104, between the mesh 104 and the patient's skin, limiting the amount of adhesion between the pressure sensitive adhesive coated side of the mesh 104 and the patient's skin 302.

Figure 18:
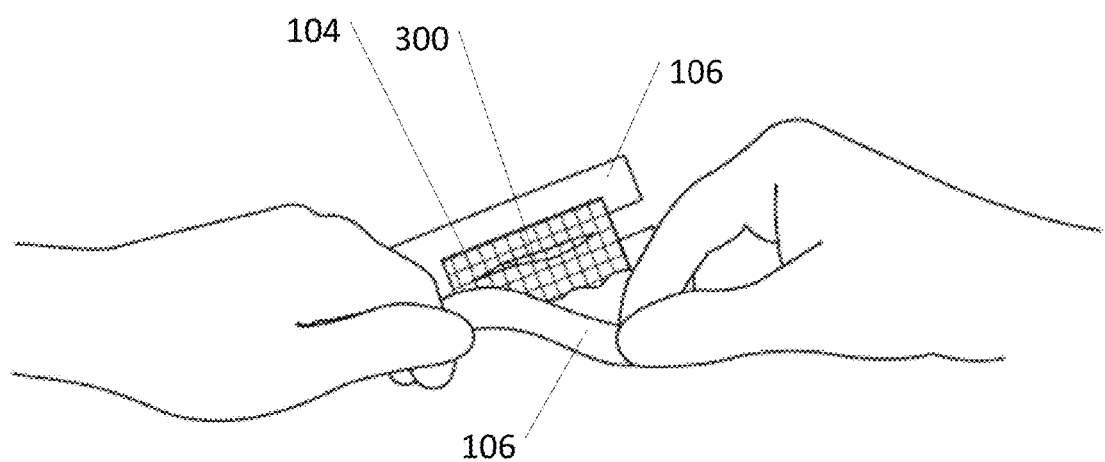
Figure 19:
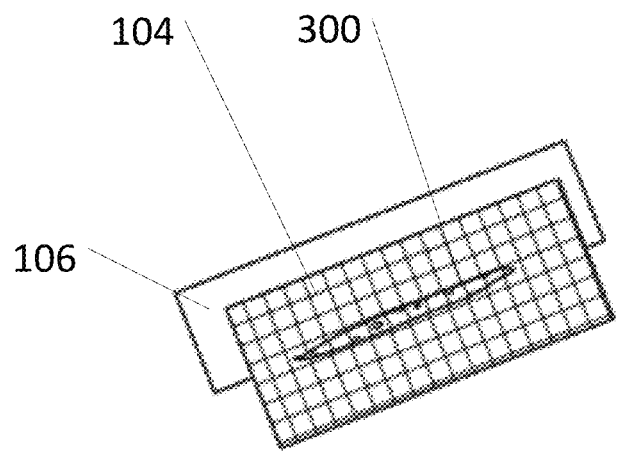
Figure 20:
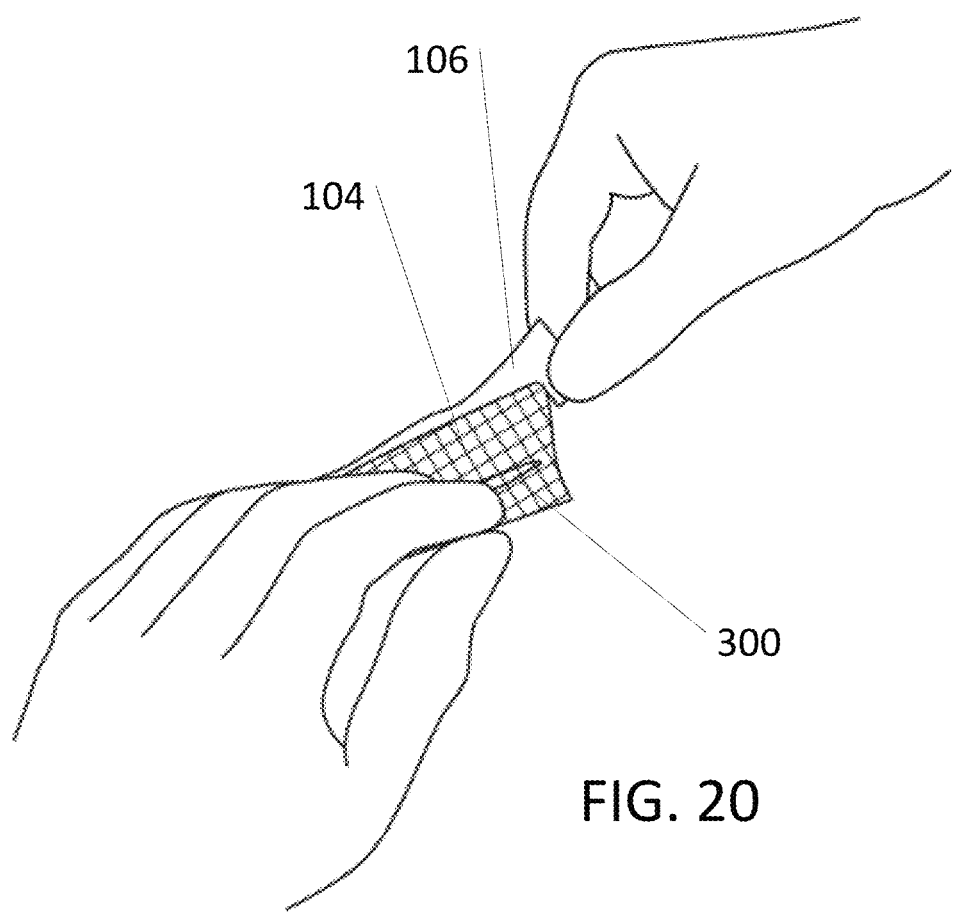

As shown in FIGS. 18-20, after the wound 300 has been approximated, the tabs 106 may each be removed and the mesh 104 may be pressed down by the user to more firmly adhere the mesh 104 to the patient's skin 302 over the wound 300. Subsequently, although not shown in the figures, a liquid, topical skin adhesive may be applied over the mesh 104 and the wound 300 to seal the wound 300 and firmly secure the mesh 104 onto the patient's skin 302 to allow the wound 300 to heal. Once cured, the liquid adhesive and mesh may provide a watertight, microbial barrier over the wound 300. The adhered mesh may distribute tension along the wound and prevent gaps from forming during the healing process.

Alternative Tab Shapes

Figure 21:
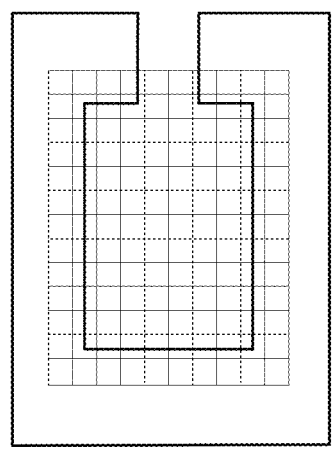
FIGS. 21-22 show examples of alternative designs for tabs of a wound closure device.
Figure 22:
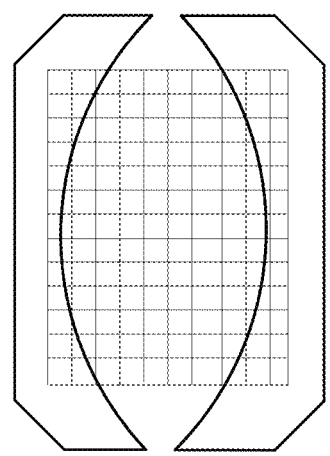

Components of the wound closure device may be configured in a wide variety of shapes and sizes. FIGS. 21 and 22 show two examples of alternative tab configurations for the wound closure device. In the example of FIG. 21, the mesh is associated with a single, generally U-shaped tab that extends along the entirety of three side edges of the mesh and partially along the fourth side of the mesh. In the example of FIG. 22, the mesh is associated with two tabs that each of crescent, curved inner edges.

Examples Only

The above-described would closure devices and methods of use are only examples. Additions, deletions, substitutions, and other changes and modifications may be made to those examples without departing from the scope or spirit of the inventions reflected in the following claims.

The invention claimed is:

1. A wound closure device, comprising:
 a release liner, the release liner comprising a plurality of score lines dividing the release liner into a unitary main body and a plurality of tabs, wherein the plurality of tabs are secured in a detachable fashion to the main body; and
 a plurality of wound closure meshes, wherein each mesh of the plurality of wound closure meshes is held in a removable fashion to the main body and at least two spaced apart tabs of the plurality of tabs, the at least two spaced apart tabs each including a portion that overlaps the mesh to which it is held and a portion that extends outwardly from the outer perimeter of the mesh to which it is held; wherein each mesh of the plurality of wound closure meshes is spaced apart from the other meshes of the plurality of wound closure meshes.

2. The wound closure device of claim 1, wherein the main body comprises a plurality of arms, wherein each mesh being held in the removable fashion to the main body comprises each mesh being held in the removable fashion to one of the plurality of arms.

3. The wound closure device of claim 2, wherein each mesh comprises a central area, wherein the plurality of arms extend across the central areas of the meshes.

4. The wound closure device of claim 3, wherein the at least two tabs of the plurality of tabs associated with each mesh extend along sides of each mesh.

5. The wound closure device of claim 4, wherein the wound closure device is configured such that each mesh can be removed from the main body while retaining the at least two tabs of the plurality of tabs extending along the sides of the mesh.

6. The wound closure device of claim 2, wherein each arm of the plurality of arms comprises a wider portion and at least one thinner portion.

7. The wound closure device of claim 6, wherein each mesh being held in the removable fashion to one of the plurality of arms comprises each mesh being held in the removable fashion to the wider portion and to the at least one thinner portion of the arm.

8. The wound closure device of claim 2 wherein each mesh of the plurality of wound closure meshes partially overlies at least one of the arms of the plurality of arms.

9. The wound closure device of claim 1, wherein the plurality of wound closure meshes comprise a plurality of self-adhering mesh patches.

10. A wound closure kit, the kit comprising:
 a wound closure device, comprising:
  a release liner, the release liner comprising a plurality of score lines dividing the release liner into a unitary main body and a plurality of tabs, wherein the plurality of tabs are secured in a detachable fashion to the main body; and
  a plurality of self-adhering wound closure mesh patches, wherein each mesh patch of the plurality of wound closure mesh patches is spaced apart from the other mesh patches of the plurality of wound closure mesh patches;
  wherein each mesh patch is held in a removable fashion to the main body and at least two spaced apart tabs of the plurality of tabs, the at least two spaced apart tabs each including a portion that overlaps the mesh patch to which it is held and a portion that extends outwardly from the outer perimeter of the mesh patch to which it is held; and an adhesive applicator, the applicator containing a liquid, topical skin adhesive.

11. The wound closure kit of claim 10, further comprising a sealed package containing the wound closure device and adhesive applicator in a sterile fashion.

12. The wound closure kit of claim 11, wherein the main body comprises a plurality of arms, wherein each mesh patch being held in the removable fashion to the main body comprises each mesh patch being held in the removable fashion to one of the plurality of arms.

13. The wound closure kit of claim 12, wherein each mesh patch comprises a central area, wherein the plurality of arms extend across the central areas of the mesh patches.

14. The wound closure kit of claim 13, wherein the at least two spaced apart tabs associated with each mesh patch extend along sides of each mesh patch.

15. The wound closure kit of claim 12 wherein each mesh patch of the plurality of self-adhering wound closure mesh patches partially overlies at least one of the arms of the plurality of arms.

16. A wound closure method, comprising:
   selecting a first wound closure mesh from a wound closure device, the wound closure device comprising:
   a release liner, the release liner comprising a plurality of score lines dividing the release liner into a unitary main body and a plurality of tabs, wherein the plurality of tabs are secured in a detachable fashion to the main body; and
   a plurality of wound closure meshes, wherein each mesh of the plurality of wound closure meshes is held in a removable fashion to the main body and at least two spaced apart tabs of the plurality of tabs, the at least two spaced apart tabs each including a portion that overlaps the mesh to which it is held and a portion that extends outwardly from the outer perimeter of the mesh to which it is held, wherein each mesh of the plurality of wound closure meshes is spaced apart from the other meshes of the plurality of wound closure meshes;
   removing the first wound closure mesh from the main body using the at least one tab removably held to the first wound closure mesh;
   positioning the first wound closure mesh on a wound; and
   removing the at least one tab removably held to the first wound closure mesh.

17. The wound closure method of claim 16, wherein removing the first wound closure mesh from the main body comprises:
   bending the wound closure device to expose an edge of at least one tab removably held to the first wound closure mesh; and
   pulling the edge of the at least one tab away from the main body to separate the at least one tab and the first wound closure mesh from the wound closure device.

18. The wound closure method of claim 17, further comprising, after positioning the first wound closure mesh on the wound, pulling on the at least one tab to approximate the wound.

19. The wound closure method of claim 18, further comprising, after approximating the wound, applying a liquid adhesive to the first wound closure mesh.

20. The wound closure method of claim 16, wherein the main body comprises a plurality of arms, wherein each mesh being held in the removable fashion to the main body comprises each mesh being held in the removable fashion to one of the plurality of arms.

21. The wound closure method of claim 20 wherein each mesh of the plurality of wound closure meshes partially overlies at least one of the arms of the plurality of arms.

* * * * *